United States Patent [19]

Smith et al.

[11] 4,087,609
[45] May 2, 1978

[54] AZIDO-TRIAZINES

[75] Inventors: Nathan L. Smith, Miami, Fla.; Vithal J. Rajadhyaksha, Mission Viejo, Calif.

[73] Assignee: Nelson Research & Development Company, Irvine, Calif.

[21] Appl. No.: 741,896

[22] Filed: Nov. 15, 1976

Related U.S. Application Data

[63] Continuation-in-part of Ser. No. 573,364, Apr. 30, 1975, abandoned.

[51] Int. Cl.$^2$ .................. C07D 251/38; C07D 251/46; C07D 251/50; C07D 251/54
[52] U.S. Cl. .................................... 544/211; 544/197; 544/208; 544/218
[58] Field of Search ........... 260/248 CS, 249.5, 249.8, 260/249.6; 544/197, 208, 211, 218

*Primary Examiner*—John M. Ford
*Attorney, Agent, or Firm*—Martin A. Voet

[57] ABSTRACT

Novel compounds having the structural formula

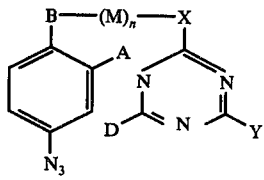

where B is NR, O, S,

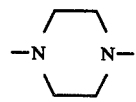

or —CH$_2$; (M)$_n$ is a saturated or unsaturated aliphatic hydrocarbon chain; X is NR, O or S; A is SO$_2$R, CN, NO$_2$ or H; Y is NR$_2$, N$_3$, halogen or SH; R is H and/or a lower alkyl group; D is N$_3$ or halogen and $n$ is 1–12.

3 Claims, No Drawings

AZIDO-TRIAZINES

BACKGROUND OF THE INVENTION

Field of the Invention

The invention relates to novel compounds. More particularly, the invention relates to novel linking compounds useful in covalently binding biologically active compounds such as enzymes and other proteins to polymeric matrices.

SUMMARY OF THE INVENTION

The invention relates to novel compounds having the structural formula

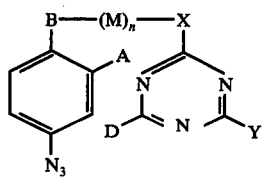

where B is NR, O, S

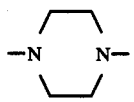

or $CH_2$, $-(M)_n$ is a saturated or unsaturated aliphatic hydrocarbon chain, X is NR, O or S; A is $SO_2R$; CN, $NO_2$ or H; Y is $NR_2$, $N_3$, halogen or SH; R is H and/or a lower alkyl group; D is $N_3$ or halogen and n is 1-12.

DETAILED DESCRIPTION OF THE INVENTION

Referring more particularly to the above structural formula, B is NR, O, S

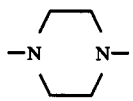

or $CH_2$ and preferably NH; $(M)_n$ is a saturated or unsaturated aliphatic hydrocarbon chain, and preferably saturated. X is NR, O or S and preferably NH; A is $SO_2R$, CN, $NO_2$ or H and preferably $NO_2$; Y is $N_3$, halogen including F, Cl and Br of SH and preferably Cl; D is $N_3$, halogen including F, Cl and Br and peferably Cl; R is H or a lower alkyl group including straight and branch chain alkyl groups having 1-8 carbon atoms and preferably 1-4 carbon atoms; and n is a positive intefer from 1-12 and preferable from about 4-8 and particularly advantageous is 6.

The saturated or unsaturated aliphatic hydrocarbon chain may be, for example, a methylene chain, $-(CH_2)-$ or an aliphatic hydrocarbon chain containing one or more carbon-carbon multiple bonds, for example, $-CH=CH-(CH_2)_n-$ or $-CH_2-(C\equiv C)_n-CH_2$ or $-CH_2-(C\equiv C)_2-CH_2-$.

A preferred class of compounds includes those compounds defined by the structural formula

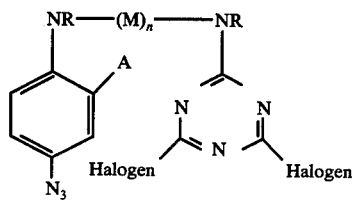

where $(M)_n$ is an aliphatic alkyl or alkenyl chain, n is a positive integer from 1-12, A is $NO_2$ or H and R is lower alkyl or H.

The preferred compound is 1-(2-nitro-4-azidophenyl)amino-6-[2-(4,6-dichloro-1,3,5-triazinyl)]aminohexane having the structural formula

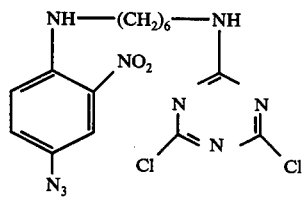

The compounds described herein are asymmetric bifunctional compounds which have utility as linking reagents. One functional moiety is a phenyl azide. The azide function may be used because of its facile conversion to a nitrene, e.g., photochemically, which inserts into covalent bonds of many organic molecules. The second functional moiety is an appropriately substituted 1,3,5-triazine which reacts with proteins and other compounds by nucleophilic displacement. The manner in which the compounds disclosed herein may be used as linking reagents is described in copending U.S. patent Application Ser. No. 573,363 filed Apr. 30, 1975, now U.S. Pat. No. 4,007,089; portions thereof relating to the manner of use of the compounds as linking reagents are hereby incorporated by this reference.

In general, the compounds of the present invention are made by first synthesizing an appropriately substituted phenyl azide which is then combined with a suitably substituted 1,3,5-triazine to form the subject compound.

Compounds encompassed by this disclosure can be made by general methods similar to the specific method described below. In general, 4-fluoro-3-nitrophenyl azide is reacted with a disubstituted aliphatic hydrocarbon having 2 to 8 and preferably 6 carbon atoms. One of these two groups may be a primary or secondary amino group which displaces the fluorine to give a 1-(2-nitro-4-azidophenyl) amino hydrocarbon derivative. Such a compound may also be a 2-nitro-4-azidophenyl hydrocarbon derivative. The hydrocarbon chain is substituted preferentially in a position para to the azido group. The terminus of the hydrocarbon chain may have an appropriate nucleophilic group, for example, a primary or secondary amino, thio or hydroxy or a substituent that can be converted to such a nucleophile without degrading the azide function, for example, a halogen or disulfide link. Compounds used in this manner may be, for example, 4-hydroxy alkylpiperazine. Once the azidophenyl hydrocarbon with the terminal nucleophile is prepared it is reacted with 2,4,6-trichloro-1,3,5-triazine or 2,4,6-triazido-1,3,5-triazine by nucleophilic displacement. In certain cases, with a terminal hydroxyl group on the hydrocarbon chain, zinc dust may be used as catalyst in the reaction with 2,4,6-trichloro-1,3,5-triazine for the displacement of a chlorine atom.

The following example is intended to illustrate the invention and is not to be construed as being limitations thereon. Temperatures are given in degrees centigrade.

EXAMPLE 1

Method of making 1-(2-nitro-4-azidophenyl)amino-6-[2-(4,6-dichloro-1,3,5-triazinyl)]-aminohexane having the structural formula

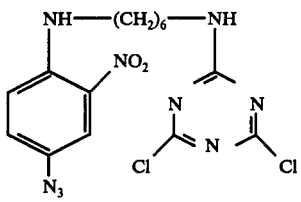

The phenyl azide portion of the molecule was made as follows: 10 g of 4-fluoro-3-nitroaniline was dissolved in 50 ml concentrated hydrochloric acid and 100 ml water with warming to 60°. The solution was then cooled to -15°. To this solution was added in 1-2 ml portions of a solution of 11 g of sodium nitrite in 40 ml water until the well-stirred reaction mixture gave a positive nitrous acid test with starch-iodine paper 5 minutes after the last addition of solution.

Excess nitrous acid was then eliminated by adding an aqueous solution of urea as needed. A solution of 4.5 g of sodium azide in 20 ml water was then added in 1-2 ml portions to the reaction mixture with vigorous stirring. The reaction mixture was then warmed to ambient termperature and stirred until evolution of nitrogen had ceased. The solution was then cooled to -10° and the precipitate of 4-fluoro-3-nitrophenylazide was filtered, the solid redissolved in ethyl acetate, filtered, concentrated at reduced pressure and recrystallized from low boiling petroleum ether. Three grams of 4-fluoro-3-nitrophenylazide was dissolved in 75 ml chloroform and added slowly to 7.2 g of 1,6-diaminohexane in 100 ml chloroform and allowed to reflux for 3 hours. 100 ml of 3N hydrochloric acid was added to the cooled reaction mixture. The aqueous layer was isolated and the pH was adjusted to 7. Sufficient sodium bicarbonate was added to make the resultant solution about half saturated with sodium bicarbonate. The resultant product 1-(2-nitro-4-azidophenyl)amino-6-aminohexane was extracted from the aqueous solution with chloroform, dried and concentrated at reduced pressure.

The final product was made by dissolving 3.9 g 1-(2-nitro-4-azidophenyl)amino-6-aminohexane and 8 g 2,4,6-trichloro-1,3,5-triazine in 50 ml of 50% saturated aqueous solution of sodium bicarbonate in 150 ml chloroform and allowing the reaction to proceed for 1.5 hours at ambient temperature with vigorous strirring. Sufficient hydrochloric acid was then added to make the aqueous layer strongly acidic and the organic phase was separated. The organic phase was dried over anhydrous sodium sulfate and concentrated at reduced pressure. The final product was extracted with 250 ml of warm low boiling petroleum ether in three portions. The petroleum ether insoluble final product may be used without further purification.

EXAMPLE 2

Method of making 1-(2-nitro-4-azidophenyl)-4-[2-(4,6-dichloro-1,3,5-triazinyloxy]ethylpiperazine having the structural formula

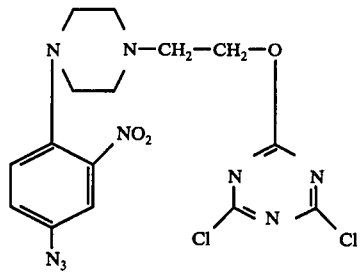

4-fluoro-2-nitrophenylazide is treated with a two fold molar excess of 4-$\beta$-hydroxyethylpiperazine in anhydrous ethanol for 24–48 hours at ambient temperature. The reaction solution is filtered and washed with water, dried, concentrated and chromatographed on silica gel to obtain 1-(2-nitro-4-azidophenyl)-4-$\beta$-hydroxyethylpiperazine in 59–61% yield.

The resultant piperazine derivative is allowed to react with 2,4,6-trichloro-1,3,5-triazine in the presence of sodium bicarbonate at ambient temperature in water or water/chloroform until the evolution of carbon dioxide has nearly ceased. Water is then added and the precipitate filtered and washed with water to obtain the final product.

EXAMPLE 3

Method of making 1-(2-nitro-4-azidophenyl)amino-4-[2-(4,6-dichloro-1,3,5-triazinyloxy)]butane having the structural formula

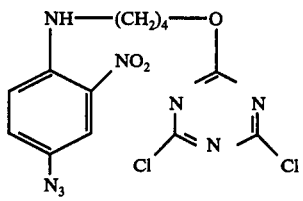

4-fluoro-2-nitrophenylazide is treated with 4-hydroxybutylamine in an organic solvent as in Example 1 to obtain 1-(2-nitro-4-azidophenyl)amino-4-hydroxybutane.

The product obtained above is refluxed with an equimolar amount of 2,4,6-trichloro-1,3,5-triazine in toluene for several hours while a stream of nitrogen gas is passed through the system to remove hydrogen chloride. Removal of toluene gives the final product.

We claim:
1. A compound having the structural formula

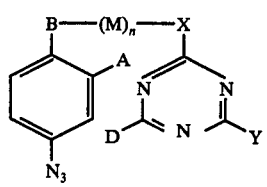

where B is sleected from the group consisting of NR, O, S and $CH_2$; $(M)_n$ is a saturated or unsaturated aliphatic hydrocarbon chain having 1-12 carbon atoms; X is selected from the group consisting of NR, O and S; A is selected from the group consisting of $SO_2R$, CN, $NO_2$ and H; Y is selected from the group consisting of $NR_2$, $N_3$, halogen and SH; R is selected from the group consisting of H and a lower alkyl group; and D is selected from the group consisting of $N_3$ and halogen.

2. A compound having the structural formula

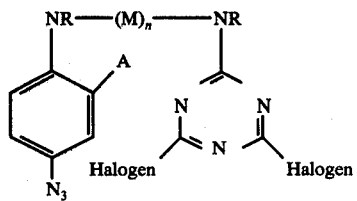

where $(M)_n$ is an aliphatic alkyl or alkenyl chain having 1-12 carbon atoms, R is selected from the group consisting of lower alkyl and H and A is selected from the group consisting of $NO_2$ and H.

3. 1-(2-nitro-4-azidophenyl)amino-6-[2-(4,6-dichloro-1,3,5-triazinyl)]-aminohexane.

* * * * *